United States Patent [19]

Bank

[11] Patent Number: 5,359,107
[45] Date of Patent: Oct. 25, 1994

[54] β-CYANOALKYLSILANE PREPARATION USING TRIORGANOPHOSPHINE COMPOUNDS AS CATALYST

[75] Inventor: Howard M. Bank, Freeland, Mich.

[73] Assignee: Dow Corning Corporation, Midland, Mich.

[21] Appl. No.: 155,883

[22] Filed: Nov. 23, 1993

[51] Int. Cl.$^5$ ................................................ C07F 7/10
[52] U.S. Cl. .................................................... 556/415
[58] Field of Search ......................................... 556/415

[56] References Cited

U.S. PATENT DOCUMENTS

| | | | |
|---|---|---|---|
| 2,906,765 | 9/1959 | Jex et al. | 556/415 |
| 2,907,784 | 10/1959 | Jex et al. | 556/415 |
| 2,908,699 | 10/1959 | Jex et al. | 556/415 |
| 3,257,440 | 6/1966 | Jex | 556/415 |
| 5,126,469 | 6/1992 | Bank | 556/415 |
| 5,247,110 | 9/1993 | Bank | 556/415 |
| 5,283,348 | 2/1994 | Bank | 556/415 |

OTHER PUBLICATIONS

Pike et al., J. Org. Chem. 24, 1939 (1959).
Ojima et al., J. Organomet. Chem. 111:43–60 (1976).
Capka et al., J. of Molecular Catalysis 11:313–322 (1981).
Capka et al., J. of Molecular Catalysis 11:323–330 (1981).

*Primary Examiner*—Paul F. Shaver
*Attorney, Agent, or Firm*—William F. Boley

[57] ABSTRACT

A process for the preparation of hydrolyzable β-cyanoalkylsilanes. More particularly, this invention relates to the catalytic addition of silicon hydrides to α,β-unsaturated olefinic nitriles to form β-cyanoalkylsilanes. The present invention uses an organic resin supported triorganophosphine, an organic resin supported triorganophosphine oxide, or triorganophosphine oxide as a catalyst.

18 Claims, No Drawings

β-CYANOALKYLSILANE PREPARATION USING TRIORGANOPHOSPHINE COMPOUNDS AS CATALYST

BACKGROUND OF INVENTION

The present invention is a process for the preparation of hydrolyzable beta-cyanoalkylsilanes. More particularly, this invention relates to the catalytic addition of silicon hydrides to α,β-unsaturated olefinic nitriles to form β-cyanoalkylsilanes. The present invention employs an organic resin supported triorganophosphine, an organic resin supported triorganophosphine oxide, or a triorganophosphine oxide as a catalyst.

Hydrolyzable beta-cyanoalkylsilanes are useful for the production of polyorganosiloxanes containing the beta-cyanoalkyl substituent. The silicon-bonded beta-cyanoalkyl radical is extremely resistant to hydrolysis and cleavage under hot, humid conditions. Therefore, beta-cyanoalkylsilanes find particular use in the preparation of polyorganosiloxanes which must be subjected to hot, humid conditions. The presence of the silicon-bonded beta-cyanoalkyl radical substituted on polyorganosiloxanes also tends to stabilize the polyorganosiloxanes against swelling induced by liquid hydrocarbons.

Jex et al., U.S. Pat. No. 2,908,699, issued Oct. 13, 1959, report the use of a phosphorous halide as a catalyst for effecting the reaction of a monoolefinic nitrile with a silane to form β-cyanoalkylsilane.

Jex et al., U.S. Pat. No. 2,906,765, issued Sept. 29, 1959, report the use of a phosphonate as a catalyst for effecting the reaction of a monoolefinic nitrile with a silane to form β-cyanoalkylsilane.

Jex et al., U.S. Pat. No. 2,907,784, issued Oct. 6, 1959, report the use of a hydrocarbyl substituted phosphine as a catalyst for effecting the reaction of a monoolefinic nitrile with a silane to form β-cyanoalkylsilanes.

Pike et al., J. Org. Chem. 24:1939 (1959), report the use of tertiary phosphines, exemplified by tributylphosphine and triphenylphosphine, to catalyze the reaction of trichlorosilane with acrylonitrile to form a β-adduct.

Jex, U.S. Pat. No. 3,257,440, issued June 21, 1966, describes the use of a catalyst comprising a hydrocarbyl substituted hydride of an element taken from Group VB of the long form of the Periodic Table as catalyst for the reaction of a silane with a monoolefinic nitrile to form a β-cyanoalkylsilane. These catalysts include unsupported triorganophosphines.

Ojima et al., J. Organomet. Chem. 111:43–60 (1976), describe a process for the reaction of α,β-unsaturated nitriles with silane to form β-cyanoalkylsilanes. In the described process tris(triphenylphosphine) chlororhodium is described as an effective catalyst.

Capka et al., J. of Molecular Catalysis 11:313–322 (1981); and J. of Molecular Catalysis 11:323–330 (1981); describe silica-supported rhodium complexes where triorganophosphine is used to couple the rhodium center to the silica. The catalysts prepared in this manner where reported to be effective hydrogenation catalysts.

Bank, U.S. Pat. No. 5,247,110, issued Sep. 21, 1993, reports the use of a phosphinoaliphaticsilane on a solid support as catalyst for the reaction of trichlorosilane with an α,β-unsaturated olefinic nitrile to form a β-cyanoalkylsilane.

The cited art does not teach the use of an organic resin supported triorganophosphine, an organic resin triorganophosphine oxide, or a triorganophosphine oxide as a catalyst for the reaction of trichlorosilane with an α,β-unsaturated olefinic nitrile to form a β-cyanoalkylsilane. The catalysts of the present process are especially useful as fixed-beds in continuous-flow processes.

SUMMARY OF INVENTION

A process for the preparation of hydrolyzable beta-cyanoalkylsilanes. More particularly, this invention relates to the catalytic addition of silicon hydrides to α,β-unsaturated olefinic nitriles to form β-cyanoalkylsilanes. The present process uses an organic resin supported triorganophosphine, an organic resin supported triorganophosphine oxide, or a triorganophosphine oxide as a catalyst.

DESCRIPTION OF INVENTION

The present invention is a process for preparation of beta-cyanoalkylsilanes described by formula:

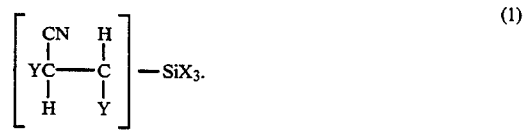
(1)

The process comprises contacting a silicon hydride described by formula

$$HSiX_3, \qquad (2)$$

with an unsaturated olefinic nitrile described by formula

$$YCH=CCN, \qquad (3)$$
         $Y$ in the presence of a catalyst selected from a group consisting of organic resin supported triorganophosphine, organic resin supported triorganophosphine oxide, or a triorganophosphine oxide at a temperature within a range of about 50° C. to about 250° C.; wherein X is a halogen and each Y is independently selected from a group consisting of hydrogen and alkyl radicals comprising one to eight carbon atoms.

The described process is applicable to the production of beta-cyanoalkylsilanes containing one silicon-bonded beta-cyanoalkyl radical, as described by Formula 1. Beta-cyanoalkylsilanes that can be made by the present process are, for example, beta-cyanoethyltrichlorosilane, beta-cyanopropyltrichlorosilane, beta-cyanobutyltrichlorosilane, beta-cyano-tert-butyltrichlorosilane, beta-cyanopentyltrichlorosilane, beta-cyanopropyltrichlorosilane, beta-cyanohexyltrichlorosilane, beta-cyanoheptyltrichlorosilane, beta-cyanooctyltrichlorosilane, alpha-methyl-beta-cylanoethyltrichlorosilane, alpha-ethyl-beta-cyanoethyltrichlorosilane, alpha-octyl-beta-cyanopropyltrichlorosilane, beta-cyanoethyltribromosilane, and beta-cyanopropyltrifluorosilane. The preferred beta-cyanoalkylsilane made by the present process is beta-cyanoethyltrichlorosilane.

The silicon hydride, described by Formula 2, contains one silicon-bonded hydrogen atom and three silicon-bonded halogen atoms. The halogen atom, X, can be selected from a group consisting of bromine, chlorine, fluorine, and iodine. The preferred halogen is chlorine.

The silicon hydride is contacted with an α,β-unsaturated olefinic nitrile described by Formula 3. The α,β-unsaturated olefinic nitrile contains substituents Y which are independently selected from a group consisting of hydrogen and lower alkyl radicals comprising from one to eight carbon atoms. For example, Y can be methyl, ethyl, propyl, butyl, tert-butyl, pentyl, hexyl, heptyl, and octyl. Examples of the α,β-unsaturated olefinic nitrile include acrylonitrile, methacrylonitrile, crotononitrile, ethylacrylonitrile, 1-cyanobutene-1, and 2-cyanooctene-1. The preferred α,β-unsaturated olefinic nitrile is acrylonitrile.

The molar ratio of the silicon hydride to the α,β-unsaturated olefinic nitrile may be varied within wide limits, however no particular advantage is derived from employing a molar excess of either reactant. The use of molar excesses of either of the two reactants is not precluded. It is preferred that the molar ratio of silicon hydride to α,β-unsaturated olefinic nitrile be within a range of about 0.5 to 1.5. In the most preferred embodiment of the invention, the molar ratio of silicon hydride to α,β-unsaturated olefinic nitrile is about 1.0.

The silicon hydride and α,β-unsaturated olefinic nitrile are contacted in the presence of a catalyst selected from a group consisting of organic resin supported triorganophosphine, organic resin supported triorganophosphine oxide, and triorganophosphine oxide.

The organic resin support can be any cross-linked hydrocarbon resin having carbon atoms capable of covalent bonding to phosphorous. For example, the support can be cross-linked resins made from copolymerized monoolefinically unsaturated hydrocarbons and polyolefinically unsaturated hydrocarbons. The monoolefinically unsaturated compounds can be, for example, styrene, 4-chlorostyrene, 3-chlorostyrene, vinyltoluenes, and trivinylbenzene. The polyolefinically unsaturated compounds may be, for example, 1,4-divinylbenzene, divinyltoluenes, and trivinylbenzene. A preferred organic resin support is cross-linked styrene/divinylbenzene copolymer resin.

Supported triorganophosphines useful in the present process are described, for example, by formula

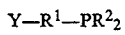

and supported triorganophosphine oxides useful in the present process are described, for example, by formula

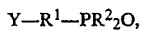

where Y is a carbon atom of the organic resin, $R^1$ is a divalent hydrocarbon radical comprising one to 10 carbon atoms, and each $R^2$ is independently selected from a group consisting of monovalent hydrocarbon radicals comprising one to 10 carbon atoms. The divalent hydrocarbon radical $R^1$ can be for example an alkylene of one to 10 carbon atoms or an arylene. Preferred is when $R^1$ is phenylene. The triorganophosphine or triorganophosphine oxide is covalently bonded to the support material through the divalent hydrocarbon radical. For example, $R^1$ can be the phenyl substituent of the styrene component of a styrene/divinylbenzene copolymer. The substituent $R^2$ can be, for example, methyl, ethyl, butyl, tert-butyl, and phenyl. A preferred supported catalyst for the present invention is a supported triorganophosphine where the organic resin support is a styrene/divinylbenzene copolymer resin, $R^1$ is a phenyl substituent of the styrene component of the copolymer resin, and each $R^2$ is phenyl.

The catalyst can be an unsupported triorganophosphine oxide as described by, for example formula $PR^2_3O$, where $R^2$ is as previously described. A preferred unsupported triorganophosphine oxide catalyst is triphenylphosphine oxide.

The amount of catalyst employed in the present process in relation to the amount of α,β-unsaturated olefinic nitrile may be varied within wide limits and is dependent upon such conditions as the temperature at which the process is run, the chemical structure of the reactants, the specific catalyst, and whether the process is run as a batch or continuous process. In general, the process can be run under conditions where the catalyst is present at about 0.1 to 50 weight percent of a mixture comprising the catalyst, the α,β-unsaturated olefinic nitrile, and the silicon hydride. Preferred is when the catalyst comprises about 0.5 to 30 weight percent of the mixture.

The silicon hydride, the α,β-unsaturated olefinic nitrile and the catalyst are contacted in a suitable reactor of standard design. The process can be run as a batch process, a semi-continuous process, or a continuous process. Preferred is a continuous process in a packed-bed reactor.

The temperature for conducting the process can be within a range of about 50° C. to about 250° C. A preferred temperature is within a range of about 80° C. to 200° C. Generally, higher temperatures allow the use of a lower catalyst concentration.

The pressure under which the process is conducted is not critical. Generally, the process can be run at a pressure within a range of about 0 psig to 1000 psig. Preferred is a pressure within a range of about 0 psig to 100 psig.

The time required for conducting the process may vary depending on the particular silicon hydride, α,β-unsaturated olefinic nitrile, temperature, and catalyst concentration employed. In general, reaction times of 0.1 to 30.0 hours are useful. A preferred reaction time is about 0.5 to 20.0 hours.

The following examples are given to illustrate the present invention. These examples are not intended to limit the present claims.

EXAMPLE 1

The ability of triphenylphosphine supported on a styrene/divinylbenzene copolymer based resin to catalyze the addition of trichlorosilane to acrylonitrile to form β-cyanoethyltrichlorosilane was evaluated in a series of runs.

The runs were conducted in sealed glass tubes purged with argon. The runs were conducted by placing a weight of catalyst as described in Table 1 into a tube, then adding to each tube 2 mL of a mixture of 5 mole percent excess trichlorosilane and acrylonitrile. The tubes were sealed then heated for 2 hours at 150° C. Unsupported triphenylphosphine was tested for comparison purposes. The test catalyst comprised triphenylphosphine supported on a cross-linked styrene/divinylbenzene copolymer resin. The supported catalyst was purchased from Alfa, Ward Hill, Mass. The supported catalyst is reported to comprise 3–7 percent phosphorous and have the formula $\{CH(C_6H_4P(C_6H_5)_2)CH_2\}_x$.

The results of these runs are presented in Table 1. The contents of individual tubes were analyzed by gas liquid chromatography (GLC) using a thermal conductivity detector (TCD). The results are expressed as the area percent (Area %) under the GLC-TCD trace for beta-cyanoethyltrichlorosilane, as a percentage of the total area under the GLC-TCD trace.

TABLE 1

Triorganophosphine Catalyzed Reaction of Trichlorosilane with Acyrlonitrile

| Catalyst | Catalyst Weight(g) | Area % β-Cyanoethyltrichlorosilane |
|---|---|---|
| Ph₃P | 0.029 | 68.4 |
| Supported Ph₃P | 0.590 | 66.2 |

EXAMPLE 2

The ability of unsupported triphenylphosphine oxide to catalyze the addition of trichlorosilane to acrylonitrile to form β-cyanoethyltrichlorosilane was evaluated. The evaluation was conducted by placing 0.037 g of triphenylphosphine oxide into a tube, then adding to the tube 2 mL of a mixture of 5 mole percent excess trichlorosilane and acrylonitrile. The tube was sealed and heated for two hours at 150° C. The composition of the tube content was analyzed as described in Example 1. The content of the tube was found to comprise 78.4 Area % β-cyanoethyltrichlorosilane.

I claim:

1. A process for preparation of beta-cyanoalkylsilanes described by formula

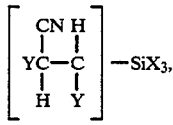

the process comprising:
contacting a silicon hydride described by formula

with an unsaturated olefinic nitrile described by formula

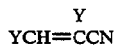

in the presence of a catalyst selected from a group consisting of organic resin supported triorganophosphine, organic resin supported triorganophosphine oxide, and triorganophosphine oxide at a temperature within a range of about 50° C. to 250° C.; where X is a halogen and each Y is independently selected from a group consisting of hydrogen and alkyl radicals comprising one to eight carbon atoms.

2. A process according to claim 1, where the temperature is within a range of 80° C. to 200° C.

3. A process according to claim 1, where the halogen is chlorine.

4. A process according to claim 1, where the silicon hydride is trichlorosilane.

5. A process according to claim 1, where the unsaturated olefinic nitrile is selected from a group consisting of acrylonitrile, methacrylonitrile, crotononitrile, ethylacrylonitrile, 1-cyanobutene-1, and 2-cyanooctene-1.

6. A process according to claim 1, where the unsaturated olefinic nitrile is acrylonitrile.

7. A process according to claim 1, where the beta-cyanoalkylsilane is beta-cyanoethyltrichlorosilane.

8. A process according to claim 1, where the silicon hydride is trichlorosilane, the olefinic nitrile is acrylonitrile and the temperature is within a range of about 80° C. to 200° C.

9. A process according to claim 1, where the mole ratio of silicon hydride to unsaturated olefinic nitrile is about 1.0.

10. A process according to claim 1, where the process is conducted for a time period in a range of about 0.1 to 30 hours.

11. A process according to claim 1, where the catalyst is an organic resin supported triorganophosphine described by formula Y—R¹—PR²₂, Y is a carbon atom of the organic resin, R¹ is a divalent hydrocarbon radical comprising one to 10 carbon atoms, and each R² is independently selected from a group consisting of monovalent hydrocarbon radicals comprising one to 10 carbon atoms.

12. A process according to claim 11, where the organic resin is a cross-linked styrene/divinylbenzene copolymer, R¹ is a phenyl substituent of the styrene component of the copolymer, and each R² is phenyl.

13. A process according to claim 1, where the catalyst is an organic resin supported triorganophosphine oxide described by formula Y—R¹—PR²₂O, Y is a carbon atom of the organic resin, R¹ is a divalent hydrocarbon radical comprising one to 10 carbon atoms, and each R² is independently selected from a group consisting of monovalent hydrocarbon radicals comprising one to 10 carbon atoms.

14. A process according to claim 13, where the organic resin is a cross-linked styrene/divinylbenzene copolymer, R¹ is a phenyl substituent of the styrene component of the copolymer, and each R² is phenyl.

15. A process according to claim 1, where the catalyst is described by formula PR²₃O and each R² is independently selected from a group consisting of monovalent hydrocarbon radicals comprising one to 10 carbon atoms.

16. A process according to claim 15, where the catalyst is triphenylphosphine oxide.

17. A process according to claim 1, where the catalyst is present at about 0.1 to 50 weight percent of a mixture comprising the catalyst, the unsaturated olefinic nitrile, and the silicon hydride.

18. A process according to claim 1, where the process is conducted as a continuous process in a packed-bed reactor.

* * * * *